United States Patent
Felix

Patent Number: 4,806,653
Date of Patent: Feb. 21, 1989

[54] PROCESS FOR PREPARATION OF IMINOOXAZOLIDINES

[75] Inventor: Raymond A. Felix, Richmond, Calif.

[73] Assignee: Stauffer Chemical Company, Westport, Conn.

[21] Appl. No.: 920,345

[22] Filed: Oct. 17, 1986

[51] Int. Cl.$^4$ .................... 01N 43/76; C07D 263/08
[52] U.S. Cl. .................... 548/234; 558/422; 562/439; 564/48; 564/49; 564/52; 564/53; 564/54; 564/55
[58] Field of Search .................... 548/234

[56] References Cited

U.S. PATENT DOCUMENTS 2,902,356  9/1959  Luckenbaugh .................... 548/234
3,686,199  8/1972  Wollweber .................... 548/234

Primary Examiner—Donald G. Daus
Assistant Examiner—Mark W. Noel
Attorney, Agent, or Firm—Joel G. Ackerman; Paul R. Martin

[57] ABSTRACT

A process of the preparation of iminooxazolidines which comprises (a) reacting a urea alcohol of the formula

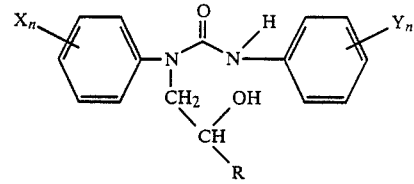

X, Y, n and R are as defined, with a dehydrating agent to form an intermediate salt compound of the formula

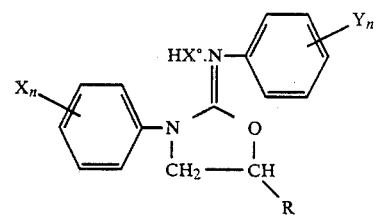

wherein X, Y, n and R are as previously defined and X° is halogen or other salt forming anion and (b) reacting said salt compound with a base to form a compound of the formula

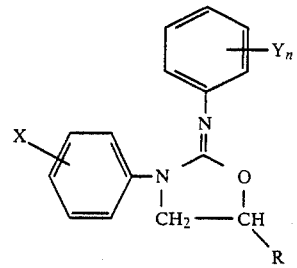

11 Claims, No Drawings

PROCESS FOR PREPARATION OF IMINOOXAZOLIDINES

BACKGROUND OF THE INVENTION

The present invention relates to a process for the preparation of certain iminooxazolidine compounds, which have been found to be effective herbicides.

Herbicides have been used for many years by farmers, commercial agricultural companies and other industries in order to eliminate weed pests and thereby increase crop yields of such staple crops as corn, soybeans, rice and the like.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the seeds or other unwanted plants from the soil. Some herbicides are effective both as pre- and post-emergence herbicides. The iminooxazolidines prepared in accordance with the process of this invention fall into that category.

DESCRIPTION OF THE INVENTION

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The iminooxazolidines prepared in accordance with the process of this invention have the formula

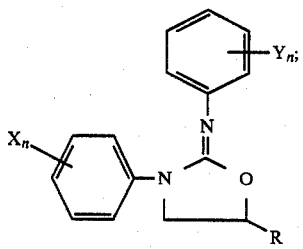

I.

wherein
X and Y are the same or different and are selected from the group consisting of hydrogen, cyano, halogen, acyl, alkyl, alkylthio, haloalkyl, haloalkylthio, alkylsulfinyl, alkoxy, carboalkoxy and haloalkoxy wherein the alkyl groups have from 1 to 5 carbon atoms;
n is the integer 1 or 2; provided that when Y is hydrogen, at least one X is other than hydrogen; and
R is hydrogen or a lower alkyl group having from 1 to 3 carbon atoms, preferably an ethyl group, and herbicidally effective salts thereof.

Representative compounds falling within the scope of the formula as set forth above include:
2-[N-(3-trifluoromethyl)phenyl]imino-3-(3-trifluoromethyl)phenyl-5-ethyl oxazolidine
2-[N-(3-trifluoromethyl)phenyl]imino-3-(3-cyano)phenyl-5-ethyl oxazolidine
2-[N-(4-chloro)phenyl]imino-3-(3-cyano)phenyl-5-ethyl oxazolidine
2-[N-(4-chloro)phenyl]imino-3-(3-trifluoromethyl)phenyl-5-ethyl oxazolidine
2-[N-(4-chloro)phenyl]imino-3-(4-chlorophenyl-5-ethyl oxazolidine
2-[N-(3-trifluoromethyl)phenyl]imino-3-(4-chloro)phenyl-5-ethyl oxazolidine
2-[N-(3,4-dichloro)phenyl]imino-3-(3-trifluoromethyl)-phenyl-5-ethyl oxazolidine
2-[N-(4-fluoro)phenyl]imino-3-(3-trifluoromethyl)phenyl-5-ethyl oxazolidine
2-[N-(4-bromo)phenyl]imino-3-(3-trifluoromethyl)phenyl-5-ethyl oxazolidine These iminooxazolidines have good herbicidal and plant growth regulating activity, when applied either pre- or post-emergence and used against annual and perennial grasses and broadleaf weeds.

The foregoing, and other compounds, of the general formula set forth above (I.) can be prepared in accordance with the process of the invention which comprises: (a) reacting a urea alcohol of the formula

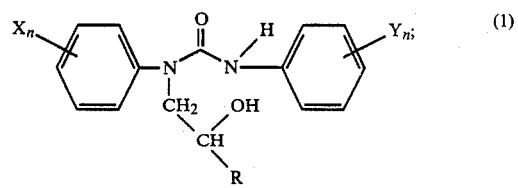

(1)

wherein
X and Y are the same or different and are selected from the group consisting of hydrogen, cyano, halogen, acyl, alkyl, alkylthio, haloalkyl, haloalkylthio, alkylsulfinyl, alkoxy, carboalkoxy and haloalkoxy wherein the alkyl groups have from 1 to 5 carbon atoms;
n is the integer 1 or 2; provided that when Y is hydrogen, at least one X is other than hydrogen; and
R is hydrogen or a lower alkyl group having from 1 to 3 carbon atoms, preferably an ethyl group, with a dehydrating agent to form an intermediate salt compound of the formula

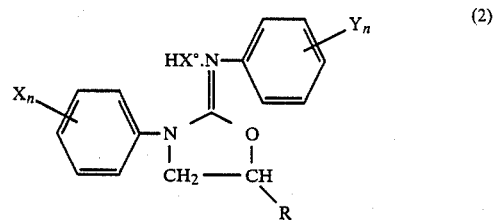

(2)

wherein X, Y, n and R are as defined above and X° is halogen or other salt forming anion and (b) reacting said salt compound with a base to form a compound of the formula

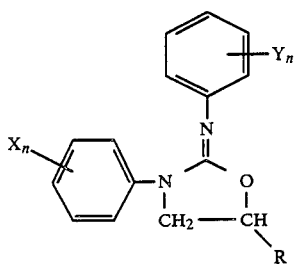

(3)

wherein X, Y, n and R are as previously defined.

The reaction sequence of the process of this invention can be represented as follows.

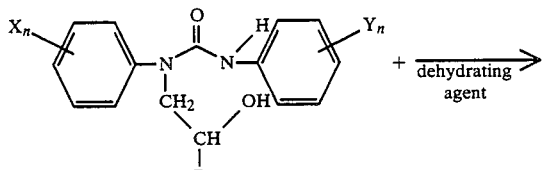

(a)

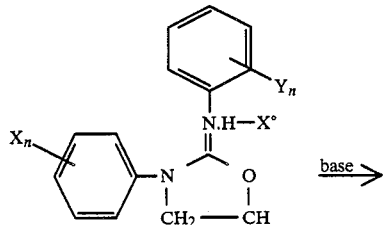

(b)

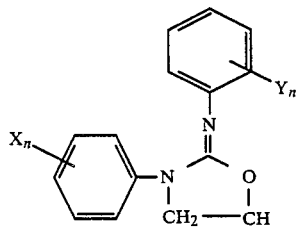

(c)

The urea alcohol used as the starting material in the process of the invention can be made by reacting an anilino alcohol of the type described in commonly assigned application Ser. No. 864,238 filed May 19, 1986, with an isocyanate, wherein the reaction is conducted at room temperature and for a period of time of about one hour. The anilino alcohol used to produce the starting urea alcohol compound of the process of this invention can in turn be made by reacting a suitable aniline with an epoxide in a manner such as is also described in application Ser. No. 864,238.

The dehydrating agent used to dehydrate the urea alcohol starting compound of this invention can be any of the conventionally known dehydrating agents, such as thionyl chloride, phosgene, phosphorus oxychloride, phosphorus pentoxide and the like. The preferred dehydrating agent for one in the process of the invention is thionyl chloride.

The dehydrating agent is preferably used in excess when used for dehydration of the urea alcohol.

The base which is used in the second step (b) of the process of the invention serves to neutralize the intermediate salt form of the compound produced as a consequence of the dehydrating step.

The base can be any of a number of commonly known bases, including pyridine, triethylamine, sodium bicarbonate, sodium hydroxide, potassium hydroxide and the like.

The preferred base for use in the process of the invention is sodium hydroxide, although the choice of base is basically an economic factor.

The process of the invention is preferably carried out at atmospheric pressure, and at ambient temperature, which will vary depending upon the particular starting compounds used. Excessive temperature results in undesirable by-products being formed.

The time of the reaction will also vary according to the starting compounds and the temperatures used.

The intermediate salt compound (b) can be isolated and has also been found to have herbicidal activity. Thus, if desired, the process can be interrupted after the dehydrating step.

Representative salt compounds which can be produced by concluding the process of the invention at the end of step (a) include:

2-[N-(3-chloro-4-methyl)phenyl]imino-3-(3-trifluoromethyl)phenyl-5-ethyl oxazolidine hydrochloride;

2-[N-(4-chloro)phenyl]imino-3-(3-trifluoromethyl)phenyl-5-ethyl oxazolidine hydrochloride;

2-[N-(4-fluoro)phenyl]imino-3-(3-trifluoromethyl)phenyl-5-ethyl oxazolidine hydrochloride;

2-[N-(4-cyano)phenyl]imino-3-(3-trifluoromethyl)phenyl-5-ethyl oxazolidine hydrochloride;

2-[N-(3-chloro-4-fluoro)phenyl]imino-3-(3-trifluoromethyl)phenyl-5-ethyl oxazolidine hydrochloride;

2-[N-(4-methoxy)phenyl]imino-3-(3-trifluoromethyl)phenyl-5-ethyl oxazolidine hydrochloride;

The process of this invention will be more fully understood by reference to the following examples which are intended to be illustrative of the process of the invention, but not limiting thereof. The products were identified by suitable analytical techniques, such as MS, NMR and IR.

EXAMPLE 1

Preparation of 2-[N-(3-Chloro-4-methyl)phenyl]imino-3-(3-trifluoromethyl)phenyl-5-ethyl oxazolidine A round-bottomed flask was obtained, equipped with an addition funnel and thermometer. Into this flask was combined 4.1 grams (g) (0.018 mole) of 1-(3-trifluoromethyl)anilino-2-butanol, 3.0 g (0.018 mole) of 3-chloro-4-methylphenyl isocyanate in 20 milliliters (ml) of methylene chloride. This mixture was stirred for one hour then stripped of methylene chloride at 40° C. The residual was identified as 1-(3-trifluoromethyl)phenyl-1-(2'-hydroxy)butyl, 3-(3-chloro-4-methyl)phenyl urea.

Thereafter, 25 ml of methylene chloride and 2.4 g thionyl chloride (0.02 mole) was added to the residual material. An exothermic reaction resulted and the reaction mixture was stirred for 0.5 hour, then allowed to cool. The methylene chloride was again stripped, and the residual material triturated with an ether/pentane mixture, yielding 6.5 g of a white solid material, which was identified by suitable analytical techniques.

Thereafter, 0.42 g of this material (0.001 mole) was combined with 0.1 g of a 50% solution of sodium hydroxide and 10 ml of methyl alcohol. The reaction mixture was then stirred at room temperature overnight, stripped, and subjected to a water work-up.

0.3 grams of the product was obtained, which was identified as such by suitable analytical techniques.

EXAMPLE 2

Preparation of 2-[N-(4-Chloro)phenyl]imino-3-(3-trifluoromethyl)phenyl-5-ethyl oxazolidine hydrochloride 4.5 grams of 1-(3-trifluoromethyl)anilino-2-butanol (0.0195 mole) was combined with 3 g of 4-chlorophenyl isocyanate (0.0195 mole) in 15 ml of toluene. The reaction mixture was then stirred and solids began to precipitate after about 1 hour. Thereafter, 10 additional ml of toluene were added and a2.6 g thionyl chloride (0.22 mole). The solids dissolved and the reaction mixture was stirred at room temperature overnight. IR analysis indicated that an HCl salt was present, and therefore 25 ml of pentane was added. A dark layer separated, and the mixture was then stirred at room temperature over the weekend, at which time solids precipitated. The solids were filtered, yielding 5.9 g of material, which was identified by suitable analytical techniques.

EXAMPLE 3

Preparation of 2-[N-(4-Chloro)phenyl]imino-3-(3-trifluoromethyl)phenyl-5-ethyl oxazolidine hydrochloride The same procedure as in the previous example was repeated, except that methylene chloride was used instead of toluene as a solvent. After the thionyl chloride addition, an exotherm resulted with gas evolution, and the reaction mixture was stirred for one hour at room temperature. It was then stripped, and triturated in ether, yielding 6.8 g of material, which was identified by suitable analytical techniques.

EXAMPLE 4

Preparation of 2-[N-(4-Chloro)phenyl]imino-3-(3-trifluoromethyl)phenyl-5-ethyl oxazolidine 1.5 g (0.01 mole) of 4-chlorophenyl isocyanate was combined with 2.25 g (0.01 mole) of 1-(3-trifluoromethyl)anilino-2-butanol in 10 ml of methylene chloride. The reaction mixture was stirred for 2 hours and at the end of that time, 1.4 g (0.01 mole) of $P_2O_5$ was added all in one portion. An exotherm resulted, and the the reaction mixture was stirred for 2 hours, then water, ether, and 100 ml of one molar NAOH was added. The phases were separated, and the aqueous phase was washed wth ether, with brine, dried and stripped, yielding 3.1 g of material identified as the product compound by suitable analytical techniques.

EXAMPLE 5

Preparation of 2-[N-(4-Fluoro)phenyl]imino-3-(3-trifluoromethyl)phenyl-5-ethyl oxazolidine 1.4 g (0.01 mole) of 4-fluorophenyl isocyanate was combined with 2.35 g (0.01 mole) of 1-(3-trifluoromethyl)anilino-2-butanol in 10 ml of toluene. The reaction mixture was stirred for 1 hour and at the end of that time, 1.8 g (0.011 mole) of $POCl_3$ in 5 ml methylene chloride was added all in one portion. The reaction mixture was stirred for 1 hour, then water, ether, and 100 ml of one molar NaOH was added. The phases were separated, and the aqueous phase was washed with ether, with brine, dried and stripped, yielding 3.5 g of material identified as the product compound by suitable analytical techniques.

Compounds which can be prepared in accordance with the same general techniques are set forth in Table 1 below.

TABLE 1

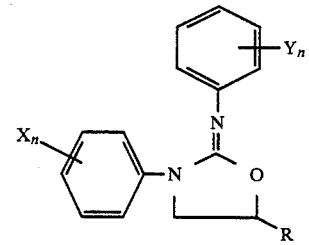

| Cmpd. No. | X | Y | R | $n_D^{30}$ or m.p. °C. |
|---|---|---|---|---|
| 1 | 3-CF$_3$ | 3-CF$_3$ | C$_2$H$_5$ | 1.5645 |
| 2 | 3-CF$_3$ | 4-Cl | C$_2$H$_5$ | 1.5680 |
| 3 | 3-cyano | 4-Cl | C$_2$H$_5$ | 1.6145 |
| 4 | 3-cyano | 3-CF$_3$ | C$_2$H$_5$ | 1.5808 |
| 5 | 4-Cl | 4-Cl | C$_2$H$_5$ | 1.6300 |
| 6 | 3-CF$_3$ | 4-Cl | C$_2$H$_5$ | 79–85 |
| 7 | 3-CF$_3$S | 4-F | C$_2$H$_5$ | 53–56 |
| 8 | 3-CF$_3$ | 3,4-Cl | C$_2$H$_5$ | 1.5675 |
| 9 | 3-CF$_3$ | 4-F | C$_2$H$_5$ | 1.5410 |
| 10 | 3-CF$_3$ | 4-Br | C$_2$H$_5$ | 1.5576 |
| 11 | 3-CF$_3$ | 4-CN | C$_2$H$_5$ | 189–196 |
| 12 | 3-CF$_3$ | 4-CH$_3$ | C$_2$H$_5$ | 1.5640 |
| 13 | 3-CF$_3$ | 4-Br | H | 1.6145 |
| 14 | 3-CF$_3$ | 3-Cl, 4-F | C$_2$H$_5$ | 55–60 |
| 15 | 3-CF$_3$ | 3-Cl, 4-OCH$_3$ | C$_2$H$_5$ | amber oil |
| 16 | 3-CF$_3$ | 3-Cl, 4-CH$_3$ | C$_2$H$_5$ | amber oil |
| 17 | 3-CF$_3$ | 3-Cl | C$_2$H$_5$ | amber oil |
| 18 | 3-CF$_3$ | 4-CF$_3$ | C$_2$H$_5$ | amber oil |
| 19 | 3-CF$_3$ | 4-ethoxycarboyl | C$_2$H$_5$ | amber oil |
| 20 | 3-CF$_3$ | 3-CF$_3$, 4-F | C$_2$H$_5$ | 95–97 |
| 21 | 3-CF$_3$ | 4-CH$_3$S | C$_2$H$_5$ | 1.5985 |
| 22 | 3-CF$_3$ | 4-SOCH$_3$ | C$_2$H$_5$ | 1.5885 |
| 23 | 3-CF$_3$ | 2-F | C$_2$H$_5$ | 1.5690 |
| 24 | 3-CF$_3$ | 3-CF$_3$, 4-Cl | C$_2$H$_5$ | 64–66 |
| 25 | 3-CF$_3$ | 3-SCH$_3$ | C$_2$H$_5$ | 1.5935 |
| 26 | 3-CF$_3$ | 2,4-F | C$_2$H$_5$ | 46–49 |
| 27 | 3-CF$_3$ | 3-F | C$_2$H$_5$ | 1.5704 |
| 28 | 3-CF$_3$ | 4-COCH$_3$ | C$_2$H$_5$ | 77–82 |
| 29 | 3-CF$_3$ | hydrogen | C$_2$H$_5$ | 1.4345 |
| 30 | 3-CF$_3$ | 4-CF$_3$O | C$_2$H$_5$ | 49–50 |

Representative intermediate salt compounds which have been prepared by the method set forth in Examples 2 and 3 include those which are set forth in Table 2 below.

TABLE 2

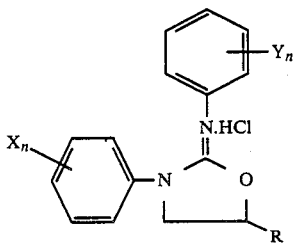

| Cmpd. No. | X | Y | R | $n_D^{30}$ or m.p. °C. |
|---|---|---|---|---|
| 1 | 3-CF$_3$ | 3-Cl, 4-CH$_3$ | C$_2$H$_5$ | 109–112 |
| 2 | 3-CF$_3$ | 4-Cl | C$_2$H$_5$ | 125–127 |
| 3 | 3-CF$_3$ | 4-Fl | C$_2$H$_5$ | 139–141 |
| 4 | 3-CF$_3$ | 4-CN | C$_2$H$_5$ | 120–124 |
| 5 | 3-CF$_3$ | 3-Cl, 4-Fl | C$_2$H$_5$ | 138–140 |
| 6 | 3-CF$_3$ | 4-OCH$_3$ | C$_2$H$_5$ | 135–138 |
| 7 | 3-CF$_3$ | 3-Cl | C$_2$H$_5$ | 118–120 |
| 8 | 3-CF$_3$ | 4-CF$_3$ | C$_2$H$_5$ | 124–127 |
| 9 | 3-CF$_3$ | 4-COOCH$_2$CH$_3$ | C$_2$H$_5$ | 124–125 |
| 10 | 3-CF$_3$ | 4-SCH$_3$ | C$_2$H$_5$ | 128–130 |
| 11 | 3-CF$_3$S | 4-Fl | C$_2$H$_5$ | 125–127 |
| 12 | 3-CF$_3$ | 4-OCF$_3$ | C$_2$H$_5$ | 125–127 |
| 13 | 3-CF$_3$ | 3-Fl | C$_2$H$_5$ | 124–125 |
| 14 | 3-CF$_3$ | 3-CF$_3$, 4-Cl | C$_2$H$_5$ | 116–119 |
| 15 | 3-CF$_3$ | 3-SC$_2$H$_5$ | C$_2$H$_5$ | 100–105 |
| 16 | 3-CF$_3$ | 2,4-Fl | C$_2$H$_5$ | 114–119 |
| 17 | 3-CF$_3$ | 3-Fl | C$_2$H$_5$ | 117–119 |
| 18 | 3-CF$_3$ | 4-COCH$_3$ | C$_2$H$_5$ | 97–100 |
| 19 | 3-CF$_3$ | hydrogen | C$_2$H$_5$ | 139–140 |

The herbicidal activity of the various compounds produced in accordance with the process of the invention is demonstrated in copending application Ser. No. 920,014, filed Oct. 17, 1986, which is incorporated herein by reference.

The compound produced in accordance with the process of the present invention show activity as herbicides in controlling the growth of undesirable vegetation when applied to such vegetation in pre- or postemergence application. The compounds are generally embodied in formulations which contain inert or occasionally active ingredients or diluent carriers in addition to the active compounds. Examples of such ingredients or carriers are water, organic solvents, surface active agents, oil, water-in-oil emulsions, wetting agents, dispersing agents, and emulsifying agents. The herbicidal formulations generally take the form of wettable powders, solutions or emulsifiable concentrates.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length.

The herbicidal compositions can also be applied to the foliage in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes. The most preferred formulations are emulsifiable concentrates which consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above can be applied to the vegetation sought to be controlled in any conventional manner either before or after the vegetation has emerged from the soil. The vegetation can be in any stage of development after emergence, ranging from seedlings to fully grown plants. Application can be achieved by any conventional technique such as the use of ground spraying equipment or aircraft-mounted sprayers. Various other application techniques will be apparent to one skilled in the pesticide art.

What is claimed is:

1. A process for the preparation of iminooxazolidines which consists of (a) reacting a urea alcohol of the formula

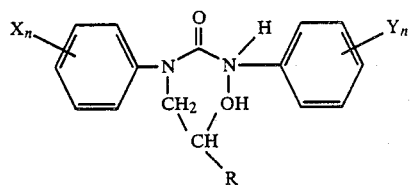

wherein
X and Y are the same or different and are selected from the group consisting of hydrogen, cyano, halogen, acyl, alkyl, alkylthio, haloalkyl, haloalkylthio, alkylsulfinyl, alkoxy, carboalkoxy and haloalkoxy wherein the alkyl groups have from 1 to 5 carbon atoms;
n is the integer 1 or 2; provided that when Y is hydrogen, at least one X is other than hydrogen; and
R is hydrogen or a lower alkyl group having from 1 to 3 carbon atoms, with a dehydrating agent selected from the group consisting of thionyl chloride, phosgene, phosphorous chlorides and phosphorous pentoxide, to form an intermediate salt compound of the formula;

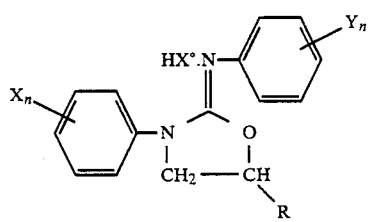

wherein X, Y, n and R are as defined above and X° is halogen or other salt forming anion from the dehydrating agent and (b) reacting said salt compound with a base to form a compound of the formula

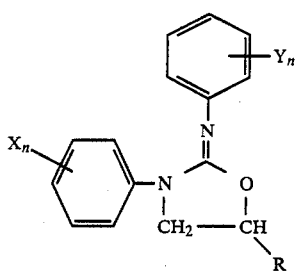

wherein n, X, Y and R are as previously defined.

2. The process of claim 1 wherein said dehydrating agent is selected from the group consisting of thionyl chloride, phosgene, phosphorous oxychloride and phosphorus pentoxide.

3. The process of claim 1 wherein the base is selected from the group consisting of pyridine, triethylamine, sodium bicarbonate, sodium hydroxide and potassium hydroxide.

4. The process of claim 1 wherein said reaction is conducted at atmospheric pressure and ambient temperatures.

5. The process of claim 2 wherein said dehydrating agent is thionyl chloride.

6. The process of claim 3 wherein said base is sodium hydroxide.

7. The process of claim 1 wherein (a) and (b) are reacted in stoichiometric ratios.

8. A process for the preparation of acid salts of iminooxazolidines which consists of (a) reacting a urea alcohol of the formula

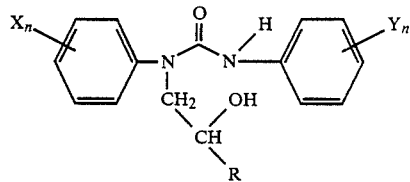

wherein
X and Y are the same or different and are selected from the group consisting of hydrogen, cyano, halogen, acyl, alkyl, alkylthio, haloalkyl, haloalkylthio, alkylsulfinyl, alkoxy, carboalkoxy and haloalkoxy wherein the alkyl groups have from 1 to 5 carbon atoms;
n is the integer 1 or 2; provided that when Y is hydrogen, at least one X is other than hydrogen; and
R is hydrogen or a lower alkyl group having from 1 to 3 carbon atoms, with a dehydrating agent selected from the group consisting of thionyl chloride, phosgene, phosphorous chlorides and phosphorous pentoxide, to form a salt compound of the formula

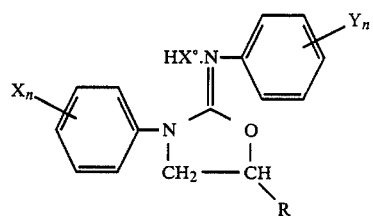

wherein X, Y, n and R are as defined above and X° is halogen or other salt forming anion from the dehydrating agent.

9. The process of claim 8 wherein said dehydrating agent is selected from the group consisting of thionyl chloride, phosgene, phosphorous oxychloride and phosphorus pentoxide.

10. The process of claim 8 wherein said reaction is conducted at atmospheric pressure.

11. The process of claim 9 wherein said dehydrating agent is thionyl chloride.

* * * * *